US006487894B1

(12) United States Patent
Dukhin et al.

(10) Patent No.: US 6,487,894 B1
(45) Date of Patent: Dec. 3, 2002

(54) METHOD FOR DETERMINING PARTICLE SIZE DISTRIBUTION AND MECHANICAL PROPERTIES OF SOFT PARTICLES IN LIQUIDS

(75) Inventors: Andrei Dukhin, Goldens Bridge, NY (US); Philip J. Goetz, Mt. Kisco, NY (US)

(73) Assignee: Dispersion Technology, Inc., Mount Kisco, NY (US)

(*) Notice: Subject to any disclaimer, the term of this patent is extended or adjusted under 35 U.S.C. 154(b) by 0 days.

(21) Appl. No.: 09/640,264

(22) Filed: Aug. 17, 2000

(51) Int. Cl.[7] .................... G01N 15/06; G01N 29/02
(52) U.S. Cl. .................... 73/61.75; 73/865.5; 73/599
(58) Field of Search ..................... 73/61.75, 61.79, 73/865.5, 69.53, 53.01, 61.41, 61.42, 61.43, 61.44, 61.45, 61.46, 61.76, 597, 599

(56) References Cited

U.S. PATENT DOCUMENTS

| | | | | |
|---|---|---|---|---|
| 4,571,693 A | * | 2/1986 | Birchak et al. | 73/24.01 |
| 6,119,510 A | * | 9/2000 | Carasso et al. | 73/61.75 |
| 6,205,848 B1 | * | 3/2001 | Faber et al. | 73/61.75 |
| 6,209,387 B1 | * | 4/2001 | Savidge | 73/24.05 |

OTHER PUBLICATIONS

Dukhin et al. Langmuir, Sep. 1996, vol. 12, pp. 4987–5003.*
Dukhin et al. Langmuir, Jul. 1999, vol. 15, pp. 6692–6706.*
Hayashi et al. Journal of the Society of Powder Technology, Japan. Dec. 2000, vol. 37, No. 7, pp. 496–504.*
Chen et al. Journal of Colloid and Interfacial Science, Feb. 1991, vol. 141, No. 2, pp. 564–577.*
U.S. patent application Ser. No. 09/108,072, Dukhin et al.
Epstein, Carhart (Epstein,P.S. and Carhart R.R., "The Absorption of Sound in Suspensions and Emulsions". J. of Acoust.Soc.Amer., 25,3,553–565 (1953).
Allegra, and Hawley (Allegra,J.R.and Hawley, S.A. "Attenuation of Sound in Suspensions and Emulsions: Theory and Experiments", J.Acoust.Soc.Amer.,51, 1545–1564 (1972).

* cited by examiner

Primary Examiner—Hezron Williams
Assistant Examiner—Michael Cygan

(57) ABSTRACT

A method is described which applies Acoustic Spectrometry to characterize both the particle size distribution and mechanical properties of the soft particles in concentrated dispersed systems. It is shown that compressibility of the soft particles can be calculated from the measured sound speed using well-known Wood expression. The value of the thermal expansion coefficient can be calculated from the measured attenuation spectra either for known particle size or together with particle size as adjustable parameter.

3 Claims, 2 Drawing Sheets

METHOD FOR DETERMINING PARTICLE SIZE DISTRIBUTION AND MECHANICAL PROPERTIES OF SOFT PARTICLES IN LIQUIDS

FIELD OF THE INVENTION

The invention relates to the determination of not only the size distribution, but also the compressibility and thermal expansion coefficients of the particles, from the measured ultrasound attenuation frequency spectra and sound speed.

BACKGROUND OF THE INVENTION

This invention deals with a particular kind of dispersed system (or colloid) that can be described as a collection of small soft particles immersed in a liquid. These particles can be either solid (latex) or liquid (emulsions). Such dispersed systems play an important role in all kind of paints, lattices, food products, paper coatings, polymer solutions, etc.

These systems have a common feature. Because of the small particle size, the total surface area of the particles is large relative to their total volume. Therefore surface related phenomena determine their behavior in various processes. This invention has particular application to dispersed systems where these surface effects are dominant, corresponding to a range of particle size up to about 10 microns. The importance of these surface effects disappears for larger particles.

The characterization of such colloids is important not only for the manufacture, but also the development of new systems with improved properties. Particle size distribution is a one of the basic notions for characterizing these dispersed systems. Several methods are known for determining particle size. Most methods are based on light, for example: light scattering; light diffraction; etc. There is a new alternative method based on ultrasound that is rapidly becoming important. This ultrasound method has a large advantage over traditional light-based techniques because it is able to characterize a concentrated system without dilution. Light-based methods usually require extreme dilution in order to make the sample sufficiently transparent for measurement. This invention deals with improvements of this ultrasound characterization technique.

There are two methods for ultrasound characterization of disperse systems: Acoustics and Electroacoustics. This invention deals only with Acoustics.

This acoustic method involves two steps. The first step is to perform an experiment on the disperse system to obtain a set of measured values for certain macroscopic properties such as temperature, pH, attenuation spectra, sound speed, etc. This invention does not deal with this step. It assumes the availability of instruments for accurate and precise measurement of the ultrasound attenuation and sound speed. One of the possible examples is described in U.S. Pat. No. 6,109,098 by Dukhin, A. S. and Goetz, P. J. "Method and device for characterizing particle size distribution and zeta potential in concentrated system by means of Acoustic and Electroacoustic Spectroscopy".

The second step is an analysis of the measured data to compute the desired microscopic properties such as particle size. Such an analysis requires three tools: a model dispersion, a prediction theory, and an analysis engine.

A "model dispersion" is an attempt to describe the real dispersion in terms of a set of model parameters including, of course, the desired microscopic characteristics. The model, in effect, makes a set of assumptions about the real world in order to simplify the complexity of the dispersion and thereby also simplify the task of developing a suitable prediction theory. For example, most particle size measuring instruments make the assumption that the particles are spherical and therefore a complete geometrical description of the particle is given by a single parameter, its diameter. Obviously such a model would not adequately describe a dispersion of carpet fibers that have a high aspect ratio and any theory based on this over-simplified model might well give incorrect results. The model dispersion may also attempt to limit the complexity of the particle size distribution by assuming that it can be described by certain conventional distribution functions, such as for example a lognormal distribution.

A "prediction theory" consists of a set of equations that describes some of the measured macroscopic properties in terms of these microscopic properties of the model dispersion. For example, a prediction theory for acoustics would attempt to describe a macroscopic property such as the ultrasound attenuation in terms of such microscopic properties as the particle size distribution, volume fraction of the dispersed phase and various physical properties of the particles and liquid.

An "analysis engine" is essentially a set of algorithms, implemented in a computer program that calculates the desired microscopic properties from the measured macroscopic data using the knowledge contained in the prediction theory. The analysis can be thought of as the opposite or inverse of prediction. Prediction describes some of the measured macroscopic properties in terms of the model dispersion. Analysis, given only the values for some of the model parameters, attempts to calculate the remaining properties by an analysis of the measured data. There are many well-documented approaches to this analysis task.

This invention suggest a new "analysis engine". The measurement part, "model dispersion" and "prediction theory" are exactly the same as described in our previous invention, U.S. Pat. No. 6,109,098. The "analysis engine" described in this patent required a certain set of input parameters for calculating the particle size distribution from the measured attenuation spectra. In particular, for dispersions of soft particles such as latexes and emulsions, it was necessary to specify a thermal expansion coefficient and compressibility of the particle materials. In many cases this data was not available, which made it impossible to apply acoustic techniques for characterizing the particle size in these dispersions.

In this invention we suggest a means to extract this unknown data about the mechanical properties of the particles from the measured attenuation spectra and sound speed. This eliminates the need to know these mechanical properties in advance. We show that the attenuation spectra and sound speed contains sufficient information to calculate both the particle size as well as the above-mentioned mechanical properties of the particles.

BRIEF SUMMARY OF INVENTION

The applicant describes a new "analysis engine" for calculating not only the particle size distribution from the measured attenuation spectra and sound speed but in addition mechanical properties such as compressibility and the thermal expansion coefficient.

DETAILED DESCRIPTION OF INVENTION

Figure 1:
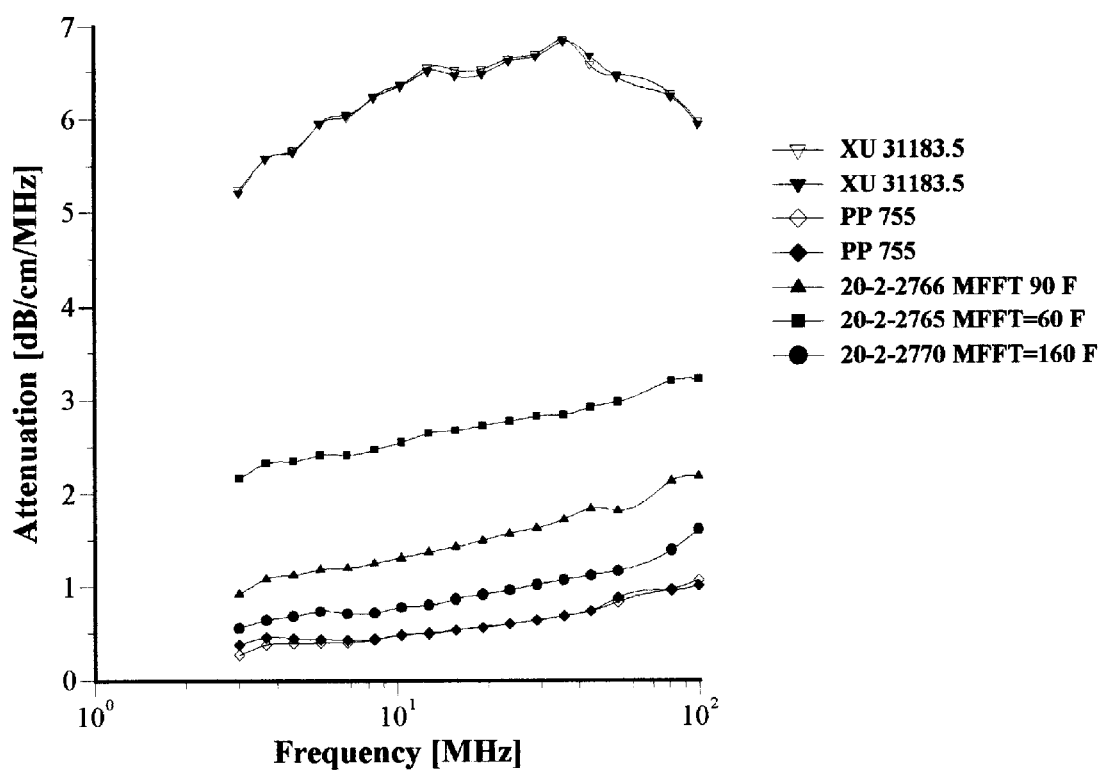
FIG. 1 shows typical attenuation spectra for a latex and an emulsion sample.

The following detailed description of the invention includes a new procedure for calculating particle size distributions from the measured ultrasound attenuation spectra. There is an available device for measuring the attenuation spectra and the sound speed of concentrated latexes and emulsions which is described in the U.S. Pat. No. 6,109,098 by Dukhin, A. S. and Goetz, P. J. "Method and device for characterizing particle size distribution and zeta potential in concentrated system by means of Acoustic and Electroacoustic Spectroscopy". FIG. 1 illustrates the attenuation spectra as measured with this commercially available device for five latex dispersions produced by Dow Chemicals for stabilizing paper coatings. Table 1 presents the measured sound speed data for the same five latex systems.

The size distributions for these five latex samples were about the same, between 150 and 200 nm. However, their mechanical properties, such as compressibility and thermal expansion are quite different. The difference in the synthesis of these latex materials leads to different "hard to soft ratios" as given in Table 1. The smaller "hard to soft ratio" correspond to samples with softer particles, and consequently we would expect both higher thermal expansion and compressibility for these samples. This relationship yields a test for verifying a theoretical algorithm suggested below.

The measured attenuation spectra and sound speed depend on the mechanical properties of the particles as well as on the particle size. This means that we can try to extract information about these mechanical properties from the measured attenuation and sound speed. First, we will show how to get information about compressibility from the sound speed. The second step will be to calculate the thermal expansion and particle size from the attenuation spectra.

The sound speed in this dispersion of small particles [$c_s$] is independent on the particle size and can be described with the so-called Wood equation [R. J. Urick "A Sound Velocity Method for Determining the Compressibility of Finely Divided Substances", J.Acous.Soc.Amer. 18, 983–087, 1947]:

$$c_s^2 = [\rho^* \gamma^*]^{-1} \quad (1)$$

where $$\rho^* = \varphi \rho_p + (1-\varphi)\rho_m \quad (2)$$

$$\gamma^* = \varphi \gamma_p + (1-\varphi)\gamma_m \quad (3)$$

where $\varphi$ is the volume fraction, $\rho$ is density, $\gamma$ is compressibility, index p corresponds to the particles, index m corresponds to the liquid.

Equations 1–3 can be used for different purposes depending on the information known about a particular system. We assume that volume fraction $\varphi$, density $\rho_m$ and compressibility $\gamma_m$ of liquid, as well as the density of the particles $\rho_p$ are known. The sound speed of the dispersion $c_s$ is also known because it is measured. This leaves only one unknown parameter—the compressibility of the particles $\alpha_p$.

Table 1 gives values for the compressibility of the latex particles as calculated from the measured sound speed. It is seen that there is a good correlation between the calculated compressibility and the "hard to soft ratio". This is a confirmation that this procedure yields reasonable values for the compressibility of the latex particles.

The second step is the calculation of the thermal expansion coefficient from the attenuation spectra. Following the most recent theory for ultrasound propagation through a dispersed system, (Dukhin, A. S. and Goetz, J. P. "Acoustic and electroacoustic spectroscopy for characterizing concentrated dispersions and emulsions", Advances in Colloid Interface Sci., 92 (2001) 73–132) we can conclude that the attenuation of ultrasound in emulsions and latexes is thermodynamic in nature if the particle size is much smaller than the wavelength. This condition, the so-called long wave requirement, is valid for relatively small particles having a size less than 10 microns and roughly within a frequency range from 1 to 100 MHz. Restricting the frequency and particle size using this long wave requirement, we can use simpler explicit expression for the thermal losses $\alpha_{th}$ obtained initially by Isakovich [Isakovich, M. A. Zh. Experimental and Theoretical Physics, 18, 907 (1948)] and confirmed later by Epstein, Carhart [Epstein, P. S. and Carhart R. R., "The Absorption of Sound in Suspensions and Emulsions", J.of Acoust.Soc.Amer., 25, 3, 553–565 (1953)], Allegra, and Hawley [Allegra, J. R. and Hawley, S. A. "Attenuation of Sound in Suspensions and Emulsions: Theory and Experiments", J.Acoust.Soc.Amer., 51, 1545–1564 (1972)]:

$$\alpha_{th} = \frac{3\varphi T c_m \rho_m \tau_m}{2a^2}\left(\frac{\beta_m}{\rho_m C_p^m} - \frac{\beta_p}{\rho_p C_p^p}\right)^2 Re\left(\frac{1}{1-jz_m} - \frac{\tau_m \tanh z_p}{\tau_p \tanh z_p - z_p}\right) \quad (4)$$

where $$z = (1+j)a\sqrt{\frac{\omega \rho C_p}{2\tau}}$$

and $\varphi$ is volume fraction, T is temperature, a is the particle size, $\rho$ is density, $\omega$ is frequency, $\tau$ thermal conductivity, $C_p$ heat capacity, $\beta$ thermal expansion, index m corresponds to the medium and index p corresponds to the particle.

In general, the prediction theory for calculating theoretical attenuation requires information about three thermodynamic properties: $\tau$ thermal conductivity, $C_p$ heat capacity and $\beta$ thermal expansion. Fortunately, it turns out that $\tau$ and $C_p$ are almost the same for all liquids except water [Dukhin, A. S. and Goetz, J. P. "Acoustic and electroacoustic spectroscopy for characterizing concentrated dispersions and emulsions", Advances in Colloid Interface Sci., 2000]. This reduces the number of required and unknown parameters to just one—the thermal expansion! This thermal expansion parameter then plays the same role in the acoustics of soft particles as the density in sedimentation or refractive index in light scattering.

Calculating the particle size from the measured attenuation spectra using Equation 4 requires information about the thermal expansion coefficient. The calculating procedure from U.S. Pat. No. 6,109,098 considers the thermal expansion coefficient as an input parameter, which is assumed to be known from some independent measurements. However, in many cases, especially latexes, it is very hard to get data on this coefficient. This has been a complication for applying acoustics for latexes and emulsions.

There are two ways to extract this thermal expansion coefficient from the attenuation spectra.

The simplest way is available when the particle size is known, and the heat capacity and heat conductance are assumed to be the same as for majority of liquids. In this case there is only one unknown parameter in equation 4, the thermal expansion coefficient of particles $\beta_p$. The thermal expansion values calculated using this simple means, assuming a particle size of 170 nm for each sample, are given in Table 1. According to the described procedure we used 18 experimental points of the attenuation spectra for calculating just one parameter—$\beta_p$. It is clear that we have an excess of experimental information. We can try to use this extra experimental data for simultaneously calculating the particle size as well as the thermal expansion. This is the second, and more complex way, to extract data from the attenuation spectra.

According to the second algorithm, we use the thermal expansion coefficient as just one adjustable parameter, in combination with the median size and standard deviation of the particle size distribution. The software uses these three adjustable parameters to minimize the fitting error between the theoretical and experimental attenuation.

Figure 2:
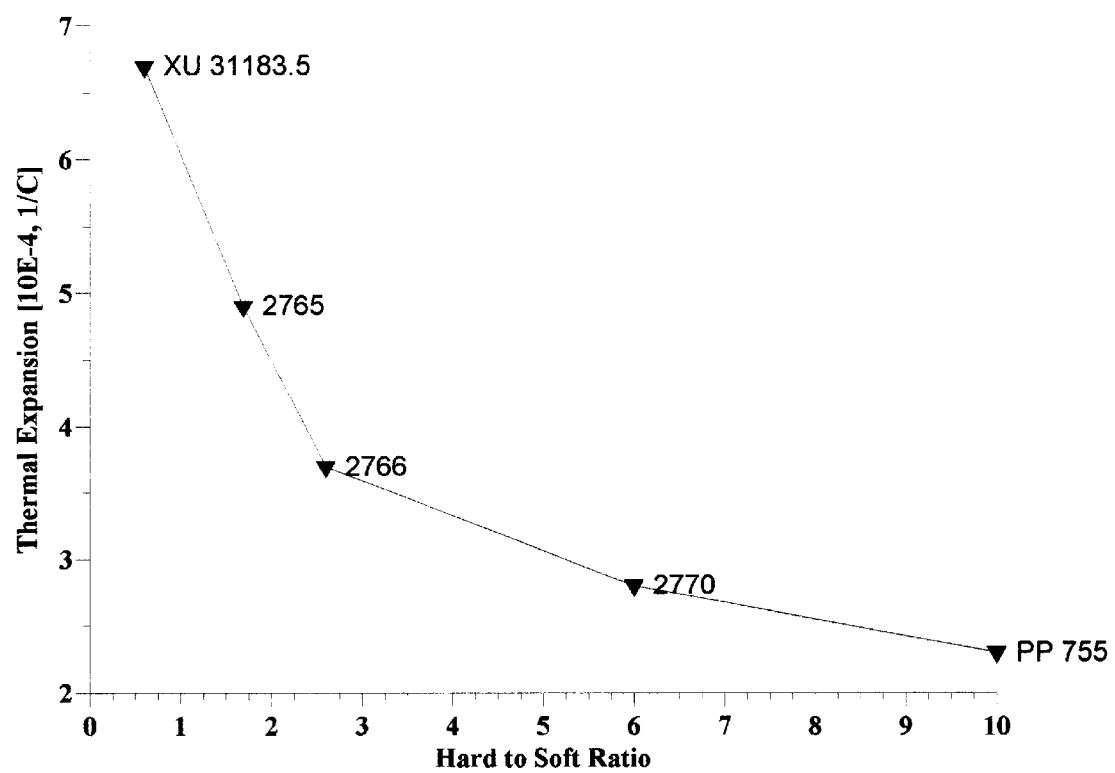
FIG. 2 shows the relationship between the calculated thermal expansion coefficients and the "hard to soft ratio".

The results of this fitting procedure are shown for all five latexes in Table 1. It is seen that resulting particle size is very close to the expected value. The thermal expansion coefficient is in good correlation with the "hard to soft ratio" as is shown in FIG. 2. This means that an attenuation spectrum contains sufficient information for extracting both, particle size and thermal expansion.

We claim:

1. Method of characterizing the mechanical properties of soft particles in liquids comprised of the measurement of both the sound speed and ultrasound attenuation spectra and subsequent calculation of the particle's compressibility from the measured sound speed and calculation of the particle's thermal expansion coefficient from the attenuation spectra, assuming a known particle size distribution.

2. Method of characterizing the mechanical properties of soft particles in liquids comprised of the measurement of both the sound speed and ultrasound attenuation spectra and subsequent calculation of the particle's compressibility from the measured sound speed and calculation of both the particle's thermal expansion coefficient and an unknown particle size distribution from the attenuation spectra.

3. Method of characterizing the mechanical properties of soft particles in liquids comprised of the measurement of only the ultrasound attenuation spectra and subsequent calculation of both the particle's thermal expansion coefficient and an unknown particle size distribution from the attenuation spectra alone.

* * * * *